United States Patent [19]

Rault et al.

[11] Patent Number: 5,332,735
[45] Date of Patent: Jul. 26, 1994

[54] COMPOUNDS OF N-BENZOYLPYROLINE

[75] Inventors: Sylvain Rault, Moult; Marie P. Foloppe, Vimoutiers; Max Robba, Paris; Michel Boulouard, Caen; Pierre Renard, Versailles; Michelle Devissaguet, Neuilly sur Seine; Gérard Adam, Le Mesnil le Roi, all of France

[73] Assignee: Adir et Compagnie, Courbevoie, France

[21] Appl. No.: 792,238

[22] Filed: Nov. 14, 1991

[30] Foreign Application Priority Data

Nov. 14, 1990 [FR] France .................. 90 14087

[51] Int. Cl.$^5$ ............. C07D 207/12; A61K 31/40
[52] U.S. Cl. ................. 524/235.5; 514/255; 514/326; 514/423; 548/530; 548/532
[58] Field of Search ............ 514/235.5, 326, 255, 514/423; 548/530, 532

[56] References Cited

U.S. PATENT DOCUMENTS

| | | | |
|---|---|---|---|
| 3,524,849 | 8/1970 | Batcho et al. | 260/239.3 |
| 3,763,183 | 10/1973 | Carabateas | 260/326.3 |
| 3,896,149 | 7/1975 | Kotone et al. | 260/326.5 |
| 4,123,544 | 10/1978 | Kornowski et al. | 424/274 |
| 4,427,587 | 1/1984 | Kaneko et al. | 260/239.3 J |
| 4,701,465 | 10/1987 | Tanaka et al. | 548/530 |
| 4,833,155 | 5/1989 | Muchowski et al. | 548/530 |
| 4,912,231 | 3/1990 | Kronenthal et al. | 548/533 |
| 5,142,065 | 8/1992 | Fischer et al. | 548/530 |

OTHER PUBLICATIONS

Chemical Abstracts, vol. 117: 111468n (1992).
Organic Chemistry, Fifth Edition, T. W. Graham Solomons, p. 793 (1992).
The Merck Index, Eleventh Edition, pp. 1189 and 1333 (1989).
Martindale, The Extra Pharmacopoeia, Thirtieth Edition, pp. 1451, 1469, 2253, 2254 (1993).
USAN and the USP Dictionary of Drug Names, United States Pharmacopeieal Convention Inc., p. 475 (1990).
Goodman and Gilman's The Pharmacological Basis of Therapeutics, Eighth Edition, pp. 131, 147, 631 (1990).
British Association of Psychopharmacology, Monographs, vol. 6, Psychopharmacology, Recent Advances and Future Prospects, Chapter 14, Neuropsychological Evaluation of Higher Cognitive Function in Animals and Man: Can Psychopharmacology Contribute to Neuropsychological Theory?, T. W. Robbins, pp. 155-169 (1985).

Primary Examiner—Nicholas S. Rizzo
Attorney, Agent, or Firm—Gordon W. Hueschen

[57] ABSTRACT

Compounds of the general formula (I):

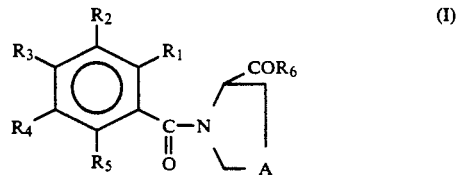

where A, $R_1$, $R_2$, $R_3$, $R_4$, $R_5$ and $R_6$ are defined in the description.

Medicinal products.

23 Claims, No Drawings

COMPOUNDS OF N-BENZOYLPYROLINE

The present invention relates to novel compounds of N-benzoylproline, the process for their preparation and the pharmaceutical compositions containing them.

Very many compounds of N-benzoylproline are known. Among them, a large number are described as simple intermediates of benzodiazepine synthesis having anti-inflammatory activity, analgesic activity, depressive activity of the central nervous system, anti-cancerous activity, antiphage activity and antibacterial activity: U.S. Pat. Nos. 3,763,183; 3,524,849; 4,427,587. U.S. Pat. No. 4,912,231 describes N-benzoyl-4-hydroxyproline compounds as synthesis intermediates.

U.S. Pat. No. 4,123,544 describes N-benzoylproline compounds which are also acetylsalicylic acid compounds and thereby claimed for their analgesic properties.

The publication J. Med. Chem 1983, 26, 9, 1333–1338 describes 1-(3,4-dichlorobenzoyl)-4-hydroxy-trans-L-proline and its lactonic compound as synthesis intermediate of anticancerous compounds.

U.S. Pat. No. 3,896,149 describes N-benzoylproline compounds as antiulceratives.

The Applicant has now discovered novel N-benzoylproline compounds which have very potent antiamnesic activity.

More particularly, the present invention relates to compounds of the general formula (I):

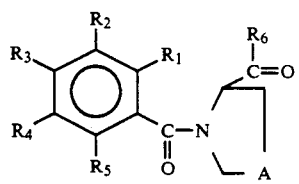

(I)

with A representing a CO, $CH_2$ or CHOH group, $R_1$, $R_2$, $R_3$, $R_4$, $R_5$, which are identical or different, representing independently of one another a hydrogen, chlorine or fluorine atom, a lower alkyl group, a cycloalkyl group with 3 to 8 carbon atoms, a hydroxyl group, a lower alkoxy group, a nitro group, a lower alkylamino group, a lower dialkylamino group, a lower phenylalkyl group, a lower phenylalkoxy group, a lower alkyl group substituted by one or more halogen atoms, or (and) alternatively two adjacent groups among $R_1$, $R_2$, $R_3$, $R_4$, $R_5$, that is to say $R_1$ and $R_2$, or $R_2$ and $R_3$ or $R_3$ and $R_4$ or $R_4$ and $R_5$ together form an $-O-CH_2-O-$, $-O-CH_2-CH_2-O-$ or $O-CH=CH-O-$ bridge, it being understood that:

one of $R_1$, $R_2$, $R_3$, $R_4$, $R_5$ can represent a nitro group only when simultaneously two adjacent groups among $R_1$, $R_2$, $R_3$, $R_4$, $R_5$ form an $-O-CH_2-O-$, or $O-CH_2-CH_2-O-$ or $-O-CH=CH-O-$ bridge, $R_1$, $R_2$, $R_3$, $R_4$, $R_5$ cannot simultaneously represent a hydrogen atom, A can represent a C=O or $CH_2$ group only when $R_1$ and $R_2$ or $R_2$ and $R_3$ or $R_3$ and $R_4$ or $R_4$ and $R_5$ together form an $-O-CH_2-O-$ or $O-CH_2-CH_2-O$ or $O-CH=CH-O-$ bridge and provided that when A represents $CH_2$:

$R_1$ cannot represent an $NO_2$ group when $R_5$ and $R_2$ each represent a hydrogen atom, $R_3$ forms with $R_4$ an $-O-CH_2-O$ group, and $R_6$ represents an $OCH_3$ group, and symmetrically $R_5$ cannot represent an $NO_2$ group when $R_1$ and $R_4$ each represent a hydrogen atom, $R_2$ forms with $R_3$ an $-O-CH_2-O-$ group, and $R_6$ represents an $OCH_3$ group, $R_6$ represents a hydroxyl group or a lower alkoxy group, an amino or $NR_7R_8$ or $-O-B-NR_7R_8$ group with B representing lower alkyl and $R_7$, $R_8$, which are identical or different, representing a hydrogen atom, a lower alkyl, or cycloalkyl or cycloalkyl or (lower alkyl), phenyl, lower phenylalkyl, substituted phenyl or substituted lower phenylalkyl group, or $R_7$ and $R_8$ form with the nitrogen which carries them a monocyclic or bicyclic heterocyclic system, each ring comprising five to six vertices and optionally integrating in its skeleton one to two hetero atoms chosen from nitrogen, oxygen or sulfur and optionally substituted by a lower alkyl or phenyl or lower phenylalkyl, or substituted phenylalkyl (lower alkyl) or substituted phenyl group, the term substituted affecting the terms phenyl and lower phenylalkyl meaning that the aromatic nucleus of these groups may be substituted by one or more lower alkyl, lower alkoxy or trifluoromethyl groups or alternatively $R_6$ forms with A an inner lactonic system thereby conferring to the compounds of formula (I) the specific structure (I'):

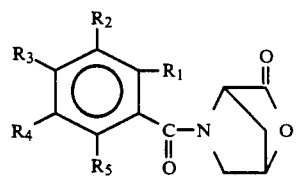

(I')

where $R_1$, $R_2$, $R_3$, $R_4$, $R_5$ have the same definition as previously provided that:

if $R_6$ and A each represent a hydroxyl group or together form an inner lactonic group (compounds of formula (I')), it is not possible to have simultaneously $R_1$, $R_4$ and $R_5$ each representing simultaneously a hydrogen atom and $R_2$ and $R_3$ each representing a chlorine atom and symmetrically $R_5$, $R_1$ and $R_2$ representing a hydrogen atom and $R_3$ and $R_4$ each representing a chlorine atom, if $R_6$ and A together form an inner lactonic group (compounds of formula (I')), at least two groups among $R_1$, $R_2$, $R_3$, $R_4$ and $R_5$ are different from the hydrogen atom, $R_1$ or $R_5$ cannot represent an acetyloxy group if simultaneously $R_2$, $R_3$, $R_4$, $R_6$ and the other group among $R_1$ and $R_5$ represent a hydrogen atom, it being understood that cycloalkyl group is understood as meaning groups with 3 to 8 carbon atoms and that lower alkyl group is understood as meaning linear or branched alkyl groups with 1 to 6 carbon atoms, as well as, if appropriate, their isomers, epimers, diastereoisomers and their addition salts with a pharmaceutically acceptable acid or base.

Among the acids which may be used to salify the compounds of general formula (I), hydrochloric, sulfuric, phosphoric, tartaric, malic, maleic, fumaric, oxalic, methanesulfuric, ethanesulfuric, camphoric, citric acids and the like may be mentioned with no limitation being implied.

Among the bases which may be used to salify the compounds of general formula (I), sodium, potassium, calcium hydroxides or organic bases such as diethylamine, benzylamine, dicyclohexylamine, arginine, or alkali or alkaline-earth metal carbonates may be mentioned with no limitation being implied.

The invention also relates to the process for obtaining the compounds of general formula (I) wherein there is used as raw material a compound of formula (II):

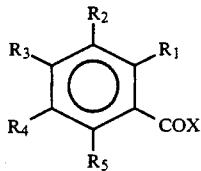
(II)

in which $R_1$, $R_2$, $R_3$, $R_4$ and $R_5$ have the same meaning as in the formula (I) and X represents a halogen atom, wherein it is treated by the compound of formula (III):

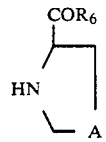
(III)

in which $R_6$ has the same meaning as in the formula (I), to give a compound of formula (I):

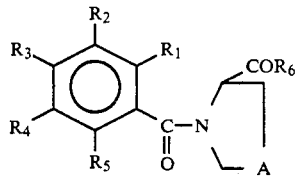
(I)

which is separated if appropriate into its isomers and which is salified, if desired, by an acid or if appropriate a pharmaceutically acceptable base,
which compound of formula (I), when $R_6$ represents an OH group, may be treated if appropriate, after optional activation of the carboxylic acid function, either by an amine of formula $NR_7R_8$ or alternatively by a compound of formula $X-B-NR_7R_8$ where B, $R_7$ and $R_8$ have the same meaning as in formula (I), and X represents a halogen atom, or alternatively by a lower aliphatic alcohol of formula $R'_6OH$ where $R'_6$ represents a lower alkyl group, to obtain a compound of formula (I) for which $R_6$ represents respectively an $NR_7R_8$ group or a lower alkyl group,
or alternatively by imidazole to obtain a compound of formula (I'),
which compound of formula (I) or (I') is purified if desired, which is separated if appropriate into its isomers and which is salified if desired by a pharmaceutically acceptable acid or base.

One specific case relates to the compounds of the invention for which A represents a C=O group. Such compounds may be advantageously obtained by treating a compound of formula (I/B):

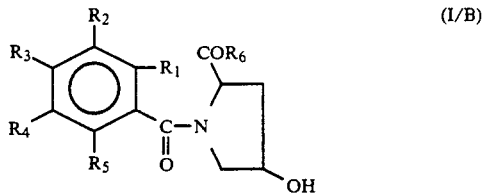
(I/B)

a specific case for compounds of formula (I) for which $R_1$, $R_2$, $R_3$, $R_4$, $R_5$ and $R_6$ have the same meaning as in formula (I) and A represents a CHOH group,
by an oxidizing agent to obtain a compound of formula (I/C):

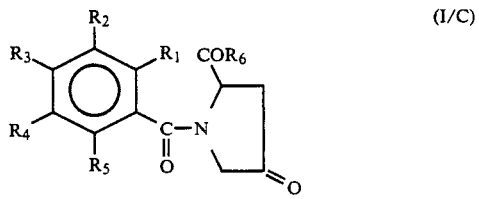
(I/C)

in which $R_1$, $R_2$, $R_3$, $R_4$, $R_5$ and $R_6$ have the same meaning as in formula (I),
which is purified and which is salified if desired, if appropriate by a pharmaceutically acceptable acid or base,
and which may be treated, when $R_6$ represents a hydroxyl group, as a function of a compound of formula (I) which it is wished to obtain, or alternatively by an amine of formula $NR_7R_8$ or by a compound of formula $X-B-NR_7R_8$ where B, $R_7$ and $R_8$ have the same meaning as in formula (I) and X represents a halogen atom, or by a lower aliphatic alcohol $R'_6OH$ where $R'_6$ represents a lower alkyl group, to obtain a compound of formula (I) for which $R_6$ represents respectively an $NR_7R_8$ group or a lower alkyl group, which is purified if necessary and the isomers of which are separated if appropriate and which are salified if desired by a pharmaceutically acceptable acid or base.

The compounds of formula (I) possess useful pharmaceutical properties.

Pharmacological study of the compounds of the invention has shown that they were of little toxicity and were very highly antagonistic of amnesia induced by scopolamine at very low doses.

The compounds of the invention therefore find their application in the treatment of diseases resulting from ischemic hypoxic and oxygen deficiency disorders and are therefore particularly recommended for improving symptoms of intellectual deficiency, the pathology of the elderly (Alzheimer's disease and mnesic disorders in general), disorders of concentration, in the treatment of constituted cerebral infarcts and in vertigos of central origin.

The compounds of the invention whose properties appeared to be the most useful are those for which A represents a CHOH group.

The subject of the present invention is also the pharmaceutical compositions containing as active ingredient at least one compound of general formula (I) or one of its addition salts with a pharmaceutically acceptable acid or base, alone or in combination with one or more pharmaceutically acceptable inert and non toxic excipients or vehicles.

Among the pharmaceutical compositions according to the invention, there may be mentioned more particularly those which are suitable for oral, parenteral or nasal administration, simple or sugared tablets, sublingual tablets, sachets, packets, hard gelatin capsules, sublingual preparations, troches, suppositories, creams, pomades, skin gels, injectable solutions and the like.

The dosage varies according to the age and the weight of the patient, the nature and the severity of the infection as well as the route of administration. The latter may be oral, nasal, rectal or parenteral.

Generally, the unit dosage ranges between 0.1 and 500 mg and may be administered 1 to 3 times per day.

The following examples illustrate the invention and do not limit it in any manner.

The $^1$H nuclear magnetic resonance spectra were achieved using TMS (tetramethylsilane) as internal standard. The clinical displacements are expressed in parts per million (p.p.m.).

The infrared spectra were obtained using a potassium bromide pastille containing about 1% of the product to be analyzed.

The examples below for which A represents a CHOH group have the general formula below:

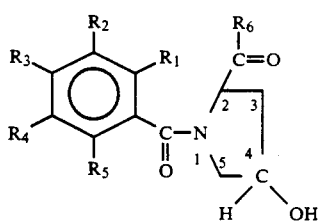

The carbon atoms numbered 2 and 4 are asymmetrical and two enantiomeric pairs therefore exist for these compounds:
TRANS-(L)- or 2S, 4R
TRANS-(D)- or 2R, 4S
CIS-(L)- or 2S, 4S
CIS-(D) or 2R, 4R.

The examples below for which A represents a CHOH group were synthesized from trans-4-hydroxy-L-proline or [(2S,4R)-(−)-4-hydroxy-2-pyrrolidine]carboxylic acid. However, the other compounds obtained from:
  trans-4-hydroxy-D-proline or [(2R,4S)-(+)-4-hydroxy-2-pyrrolidine]carboxylic acid,
  cis-4-hydroxy-D-proline or [(2R,4R)-(+)-4-hydroxy-2-pyrrolidine]carboxylic acid,
  cis-4-hydroxy-L-proline or [(2S,4S)-(−)-4-hydroxy-2-pyrrolidine]carboxylic acid,
are part of the invention in the same way as the preceding compounds.

When A represents a $CH_2$ group or a CO group, two isomers called L or D (R or S) exist. The corresponding examples below were carried out using (L)-proline or these compounds. The two series of isomers nevertheless are an integral part of the invention.

The preparations are not part of the invention but are useful for carrying out the synthesis of the compounds of the invention.

PREPARATION 1: 4,5-METHYLENEDIOXY-2-NITROBENZOYL CHLORIDE

STAGE A: 4,5-METHYLENEDIOXY-2-NITROBENZOIC ACID 30 g (0.18 mole) of piperonylic acid are added with care to 200 ml of nitric acid (d=1.42). After a first addition of 5 g, the reaction is started by heating and by vigorously stirring the reaction mixture at 50° C. The addition of the remaining 25 g is carried out in small fractions. At the end of the addition, the reaction mixture is left stirring for 2 hours. Then 200 ml of water are added, the insoluble reaction product is spun, washed with 100 ml of water and then dissolved in a saturated aqueous solution of sodium bicarbonate. The insoluble compounds are removed. The filtrate is acidified at 0° C. and the precipitate is collected and then spun, washed with water and dried.
Yield: 67%
Melting point: 172° C.
Spectral characteristics:
νCO 1710 cm$^{-1}$
νNO$_2$ 1515 and 1335 cm$^{-1}$

STAGE B: 4,5-METHYLENEDIOXY-2-NITROBENZOYL CHLORIDE 5 g (0.23 mole) of 4,5-methylenedioxy-2-nitrobenzoic acid are suspended in 50 ml of thionyl chloride and refluxed for 2 hours. The solution obtained is concentrated under reduced pressure. The residual oil crystallizes immediately after the addition of 50 ml of petroleum ether. The crystals are spun and recrystallized in ether.
Yield: 90%
Melting point: 70° C.
Spectral characteristics:
Infrared:
νC=O: 1775 cm$^{-1}$
Percentage composition:
  Calculated: C: 41.85 H: 1.75 N: 6.10 N: 15.44 Found: C: 41.78 H: 1.67 N: 5.94 N: 15.32

PREPARATION 2: 3,4-DIMETHOXYBENZOYL CHLORIDE 20 g (0.1 mole) of 3,4-dimethoxybenzoic acid are suspended in 170 ml of thionyl chloride and refluxed for 2 hours. The solution is concentrated under reduced pressure. The residual oil crystallizes immediately after the addition of petroleum ether. The crystals are spun and washed with petroleum ether.
Melting point: 70° C.
Spectral characteristics:
Infrared:
νC=O: 1760 cm$^{-1}$

PREPARATION 3: 3,4-METHYLENEDIOXYBENZOYL CHLORIDE 20 g (0.12 mole) of piperonylic acid are suspended in 170 ml of thionyl chloride and refluxed for 2 hours. The solution is concentrated under reduced pressure. The residual oil crystallizes immediately after the addition of petroleum ether. The crystals are spun and washed with petroleum ether.
Melting point: 80° C.
Spectral characteristics:

Infrared:
νC=O: 1750 cm$^{-1}$

PREPARATION 4: 3,4,5-TRIMETHOXYBENZOYL CHLORIDE 10 g of (0.047 mole) of 3,4,5-trimethoxybenzoic acid are suspended in 120 ml of thionyl chloride and refluxed for 2 hours. The solution is concentrated under reduced pressure. The residual oil crystallizes immediately after the addition of petroleum ether. The crystals are spun and washed with petroleum ether.
Melting point: 80° C.
Spectral characteristics:
Infrared:
νC=O: 1750 cm$^{-1}$

PREPARATION 5: 4-HYDROXYBENZOYL CHLORIDE 10 g (0.072 mole) of 4-hydroxybenzoic acid is placed in 100 cm$^3$ of toluene. 20 g of phosphorus pentachloride are added in small portions and the mixture is stirred under slight heating for two hours. It is concentrated under reduced pressure. The residue is triturated in petroleum ether, spun, dried, washed with water and then dried again. 3,4-dihydroxybenzoyl chloride is similarly obtained from 3,4-dihydroxybenzoic acid.

PREPARATION 6: 3,4-ETHYLENEDIOXYBENZOYL CHLORIDE

STAGE A: 3,4-ETHYLENEDIOXYBENZOIC ACID 10 g (0.06 mole) of 1,4-benzodioxane-6-carboxaldehyde in 250 ml of water are heated to 70°-80° C. by means of a water bath. A solution of 13.4 g (0.084 mole) of potassium permanganate in solution in 300 ml of water is added dropwise into this emulsion over 45 minutes. After this addition, the stirring and the heating are maintained for 1 hour. 10% potassium hydroxide is then added in sufficient amount to make the solution alkaline. The mixture, still hot, is filtered, the manganese dioxide formed is washed 3 times with 50 ml of water. The filtrate and the washings are combined and then acidified by means of 12N hydrochloric acid. The white precipitate formed is spun and washed with water and dried.
Yield: 76%
Melting point: 142° C.
Spectral characteristics:
νCO: 1670 cm$^{-1}$

STAGE B: 3,4-ETHYLENEDIOXYBENZOYL CHLORIDE

By carrying out the procedure as in Stage B of Preparation 1, but replacing piperonylic acid by the 3,4-ethylenedioxybenzoic acid formed in the preceding stage, the title product is obtained.
Melting point: 103° C.

PREPARATION 7: 4-TRIFLUOROMETHYLBENZOYL CHLORIDE

By carrying out the procedure as in Preparation 1, Stage B, but replacing 4,5-methylenedioxy-2-nitrobenzoic acid by 4-trifluoromethylbenzoic acid, the title product is obtained.

PREPARATION 8: 4-CHLOROBENZOYL CHLORIDE

By carrying out the procedure as in Preparation 1, Stage B, but replacing 4,5-methylenedioxy-2-nitrobenzoic acid by 4-chlorobenzoic acid, the title product is obtained.

PREPARATION 9: 2-BENZYLBENZOYL CHLORIDE

By carrying out the procedure as in Preparation 1, Stage B, but replacing 4,5-methylenedioxy-2-nitrobenzoic acid by 2-benzylbenzoic acid, the title product is obtained.

PREPARATION 10: 4-BENZYLOXYBENZOYL CHLORIDE

By carrying out the procedure as in Preparation 1, Stage B, but replacing 4,5-methylenedioxy-2-nitrobenzoic acid by 4-benzyloxybenzoic acid, the title product is obtained.

PREPARATION 11: 3,5-DI-TERT-BUTYL-4-HYDROXYBENZOYL CHLORIDE

By carrying out the procedure as in Preparation 5, but replacing 4,5-methylenedioxy-2-nitrobenzoic acid by 3,5-di-tert-butyl-4-hydroxybenzoic acid, the title product is obtained.

PREPARATION 12: 6-BENZO-[1,4]-DIOXINCARBONYL CHLORIDE

By carrying out the procedure as in Preparation 5, but replacing 4,5-methylenedioxy-2-nitrobenzoic acid by 6-benzo-[1,4]dioxincarboxylic acid, the title product is obtained.

PREPARATION 13: 2,3-METHYLENEDIOXYBENZOYL CHLORIDE

By carrying out the procedure as in Preparation 1—Stage B, but replacing 4,5-methylenedioxy-2-nitrobenzoic acid by 2,3-methylenedioxybenzoic acid, the title product is obtained.

PREPARATION 14: 2,3-ETHYLENEDIOXYBENZOYL CHLORIDE

By carrying out the procedure as in Preparation 2—Stage B, but replacing 4,5-methylenedioxy-2-nitrobenzoic acid by 2,3-ethylenedioxybenzoic acid, the title product is obtained.

PREPARATION 15: 4-METHOXYBENZOYL CHLORIDE 2 equivalents of thionyl chloride and 0.1 g of aluminum chloride are added to 10 g (0.06 mole) of 4-methoxybenzoic acid in suspension in 60 ml of petroleum ether. This reaction mixture is refluxed for 5 hours. The solution is concentrated under reduced pressure. The residual oil crystallizes in the presence of petroleum ether at 0° C.
Melting point: 24° C.
Spectral characteristics:
Infrared:
C=O band at 1770 cm$^{-1}$

EXAMPLE 1: 4-HYDROXY-1-(4,5-METHYLENEDIOXY-2-NITROBENZOYL)PYRROLIDINE-2-CARBOXYLIC ACID (TRANS FORM)

In a 2-liter three-necked round-bottomed flask equipped with 2 bromine funnels and a thermometer, a solution of 32 g (0.22 mole) of trans-4-hydroxyproline is cooled in an ice bath in 200 ml of water which is vigorously stirred. 22.8 g (0.1 mole) of 4,5-methylenedioxy-2-nitrobenzoyl chloride obtained in Preparation 1 in solution in 150 ml of acetone are added dropwise, by means of the bromine funnel. Simultaneously, a 40% solution of sodium hydroxide is also added dropwise so that the pH of the reaction mixture remains alkaline. The stirring is continued after the end of the addition for 20 minutes at room temperature. The acetone is removed under vacuum without exceeding 40° C. The aqueous solution is then acidified and then left for 24 hours at room temperature. The crystals formed are spun, washed with water, dried and recrystallized in isopropanol.
Yield: 75%
Melting point: 230° C.
Spectral characteristics:
$\nu$CO: 1730 and 1620 cm$^{-1}$
$^1$H nuclear magnetic resonance:
O—$\underline{CH_2}$—O $\delta$=6.25 ppm
=C$\underline{H}$—C=O $\delta$=6.80 ppm
C$\underline{H}$—CNO$_2$ $\delta$=7.65 ppm
Percentage composition:
  Calculated: C: 48.15 H: 3.73 N: 8.63 Found: C: 47.91 H: 3.63 N: 8.53

EXAMPLE 2:
4-HYDROXY-1-(4,5-METHYLENEDIOXY-2-NITROBENZOYL)PYRROLIDINE-2-CARBOXAMIDE 5 g (0.015 mole) of trans-4-hydroxy-1-(4,5-methylenedioxy-2-nitrobenzoyl)pyrrolidine-2-carboxylic acid obtained in Example 1 are suspended in 130 ml of acetonitrile at room temperature and then 2.25 ml (0.015 mole) of triethylamine are added. After 30 minutes of stirring starting from the end of the addition, 1.5 ml (0.015 mol) of ethyl chloroformate are added into the suspension previously cooled at 5° C. The reaction mixture is again stirred for 30 minutes. Ammonia is bubbled through this solution, the temperature of which is maintained between 0° C. and 5° C. A precipitate appears. It is spun, washed with ether and recrystallized in acetonitrile.
Yield: 84%
Melting point: 264° C.
Spectral characteristics:
$\nu$OH: 3440 cm$^{-1}$
$\nu$NH$_2$: 3355, 3315 and 3290 cm$^{-1}$
$\nu$C=O: 1655 and 1615 cm$^{-1}$
$^1$H nuclear magnetic resonance:
O—$\underline{CH_2}$—O $\delta$=6.25 ppm
=C$\underline{H}$—C=O $\delta$=7.08 ppm
C$\underline{H}$—CNO$_2$ $\delta$=7.70 ppm
Percentage composition:
  Calculated: C: 48.30 H: 4.05 N: 12.99 Found: C: 48.38 H: 4.04 N: 13.11

EXAMPLE 3:
4-OXO-1-(4,5-METHYLENEDIOXY-2-NITROBENZOYL)PYRROLIDINE-2-CARBOXYLIC ACID 15 ml of Jones reagent (aqueous chromic and sulfuric acid solution) are added dropwise to a solution of 8 g (0.025 mole) of trans-4-hydroxy-1-(4,5-methylenedioxy-2-nitrobenzoyl)pyrrolidine-2-carboxylic acid obtained in Example 1, in 500 ml of acetone. The reaction mixture is stirred for 2 hours. The acetone is removed under vacuum. The residue obtained is taken up in water. The precipitate is separated, dried and recrystallized in a V/V mixture of methanol and petroleum ether.
Yield: 90%
Melting point: 250° C.
Spectral characteristics:
Infrared:
$\nu$C=O 1760 and 1735 cm$^{-1}$
Nuclear magnetic resonance:
O—$\underline{CH_2}$—O $\delta$=6.25 ppm
=C$\underline{H}$—C=O $\delta$=6.93 ppm
C$\underline{H}$—CNO$_2$ $\delta$=7.70 ppm
Percentage composition:
  Calculated: C: 48.46 H: 3.13 N: 8.69 Found: C: 48.29 H: 3.35 N: 8.49

EXAMPLE 4:
(TRANS)4-HYDROXY-1-(3,4-DIMETHOXYBENZOYL)PYRROLIDINE-2-CARBOXYLIC ACID

By carrying out the procedure as in Example 1, but using the 3,4-dimethoxybenzoyl acid chloride obtained in Preparation 2 instead of 4,5-methylenedioxy-2-nitrobenzoyl chloride, the title product is obtained.
Yield: 60%
Melting point: 212° C.
Spectral characteristics:
$\nu$C=O at 1700 cm$^{-1}$
Nuclear magnetic resonance:
OCH$_3$ $\delta$=3.80 ppm
Percentage composition:
  Calculated: C: 56.95 H: 5.80 N: 4.74 Found: C: 56.72 H: 5.89 N: 4.43

EXAMPLE 5:
1-(3,4-METHYLENEDIOXYBENZOYL)PYRROLIDINE-2-CARBOXYLIC ACID

By carrying out the procedure as in Example 1, but using proline instead of trans-4-hydroxyproline and the 3,4-dimethoxybenzoyl chloride obtained in Preparation 3 instead of 4,5-methylenedioxy-2-nitrobenzoyl chloride, the title product is obtained.
Yield: 65%
Melting point: 164° C.
Spectral characteristics:
$\nu$C=O at 1730 and 1620 cm$^{-1}$
Nuclear magnetic resonance:
C$\underline{H}$—COOH $\delta$=4.4 ppm
O—$\underline{CH_2}$—O $\delta$=6.07 ppm
aromatics: unresolved complex at 7 ppm
Percentage composition:
  Calculated: C: 59.31 H: 4.97 N: 5.32 Found: C: 59.31 H: 5.04 N: 5.19

EXAMPLE 6:
4-HYDROXY-1-(3,4-METHYLENEDIOXYBENZOYL)PYRROLIDINE-2-CARBOXYLIC ACID
(trans form)

By carrying out the procedure as in Example 1 and by replacing 4,5-methylenedioxy-2-nitrobenzoyl chloride by the 3,4-methylenedioxybenzoyl chloride obtained in Preparation 3, the title product is obtained.
Recrystallization: isopropanol
Yield: 70%
Melting point: 230° C.
Spectral characteristics:
Infrared:
$\nu$C=O at 1740 and 1630 cm$^{-1}$
Nuclear magnetic resonance:
O—$\underline{CH_2}$—O $\delta$=6.09 ppm
aromatics: unresolved complex at 7 ppm

EXAMPLE 7: 4-HYDROXY-1-(3,4-DIMETHOXYBENZOYL)-PYRROLIDINE-2-CARBOXAMIDE 1.1 equivalents of triethylamine are added to 3 g (0.01 mole) of the trans-4-hydroxy- 1-(3,4-dimethoxybenzoyl)pyrrolidine-2-carboxylic acid obtained in Example 4 in suspension of 200 ml of acetone at 0° C. The reaction mixture is stirred for 20 minutes and then 1.1 equivalents of ethyl chloroformate are added while maintaining the temperature between 0° C. and 5° C. After stirring for 20 minutes, the mixture is filtered and ammonia is bubbled through the solution. The precipitate formed is separated, the acetone is removed under vacuum and the product obtained is recrystallized in water.
Yield: 70%
Melting point: 240° C.
Spectral characteristics:
Infrared:
$\nu C=O$: 1675 and 1615 cm$^{-1}$
Nuclear magnetic resonance:
O—CH$_3$ $\delta = 3.8$ ppm

EXAMPLE 8: 4-HYDROXY-1-(3,4,5-TRIMETHOXYBENZOYL)-PYRROLIDINE-2-CARBOXYLIC ACID

By carrying out the procedure as in Example 1, but using the 3,4,5-trimethoxybenzoyl chloride obtained in Preparation 4 instead of 4,5-methylenedioxy-2-nitrobenzoyl chloride, the title product is obtained.
Yield: 50%
Melting point: 202° C.
Spectral characteristics:
Infrared:
$\nu C=O$: 1740 cm$^{-1}$
Nuclear magnetic resonance:
O—CH$_3$ $\delta = 3.8$ ppm
aromatics: $\delta = 6-8$ ppm
Percentage composition:
Calculated: C: 55.38 H: 5.88 N: 4.30 Found: C: 55.34 H: 5.74 N: 4.31

EXAMPLE 9: 4-HYDROXY-1-[3,4-METHYLENEDIOXYBENZOYL]PYRROLIDINE-2-CARBOXAMIDE 1.1 equivalents of triethylamine are added to 4.5 g (0.016 mol) of the 4-hydroxy-1-[3,4-methylenedioxybenzoyl]pyrrolidine-2-carboxylic acid obtained in Example 5 suspended in 130 ml of acetonitrile at 0° C. The reaction mixture is stirred for 20 minutes and then 1.1 equivalents of ethyl chloroformate are added while maintaining the temperature between 0° and 5° C. After stirring for 20 minutes, ammonia is bubbled through the reaction mixture. The precipitate formed is separated. The filtrate is removed under vacuum, the precipitate obtained is recrystallized in acetonitrile.
Yield: 47%
Melting point: 176° C.
Spectral characteristics:
Infrared:
$\nu C=O$: 1670 and 1600 cm$^{-1}$
Nuclear magnetic resonance:
O—CH$_2$—O $\delta = 6.08$ ppm
aromatics = 7.01 ppm

EXAMPLE 10: 1-[3,4-ETHYLENEDIOXYBENZOYL]-4-HYDROXYPYRROLIDINE-2-CARBOXYLIC ACID

By carrying out the procedure as in Example 1, but replacing 4,5-methylenedioxy-2-nitrobenzoyl chloride by the 3,4-ethylenedioxybenzoyl chloride obtained in Preparation 6, the title product is obtained.
Yield: 70%
Melting point: 142° C.
Spectral characteristics:
Infrared:
$\nu C=O$: 1725 cm$^{-1}$
Nuclear magnetic resonance: (DMSO-d$_6$)
O—CH$_2$—CH$_2$—O $\delta = 4.25$ ppm
aromatics: 6.95 ppm

EXAMPLE 11: METHYL 4-HYDROXY-1- 8 3,4-METHYLENEDIOXYBENZOYL]PYRROLIDINE-2-CARBOXYLATE 0.06 mole of 4-hydroxy-1-[3,4-methylenedioxybenzoyl]pyrrolidine-2-carboxylic acid obtained in Example 6 in a mixture of 150 ml of methanol and 5 ml of sulfuric acid (d=1.84) are refluxed for 7 hours. Methanol is removed under vacuum. The residue is taken up in ethyl acetate, the organic phase is washed by means of a saturated solution of sodium bicarbonate and then with water until a neutral pH is obtained. The ethyl acetate is dried over magnesium sulfate and removed under vacuum. The compound obtained is recrystallized in an ether/acetone mixture.
Yield: 72%
Melting point: 142° C.
Spectral characteristics:
Infrared:
$\nu OH$: 3430 cm$^{-1}$
$\nu C=O$: 1730 cm$^{-1}$
Nuclear magnetic resonance: (DMSO-d$_6$)
$\delta = 3.65$ ppm, CH$_3$
$\delta = 6.09$ ppm, O—CH$_2$—O
$\delta = 7.03$ ppm, aromatics

EXAMPLE 12: METHYL 4-HYDROXY-1-[3,4-DIMETHOXYBENZOYL]-PYRROLIDINE- 2-CARBOXYLATE

By carrying out the procedure as in Example 11, but replacing 4-hydroxy-1-[3,4-methylenedioxybenzoyl]-pyrrolidine-2-carboxylic acid by 1-[3,4-dimethoxybenzoyl]pyrrolidine-2-carboxylic acid (Example 4), the title product is obtained. (recrystallization solvent: isopropanol).
Yield: 50%
Melting point: 174° C.
Spectral characteristics:
Infrared:
$\nu OH$: 3340 cm$^{-1}$
$\nu CO$: 1750 cm$^{-1}$
$\nu CO$: 1610 cm$^{-1}$
Nuclear magnetic resonance: (DMSO-d$_6$)
$\delta = 3.65$ ppm, CH$_3$ (COOCH$_3$)
$\delta = 3.80$ ppm, 2 OCH$_3$
$\delta = 7.04$ ppm, aromatics

EXAMPLE 13: METHYL 4-HYDROXY-1-[4,5-METHYLENEDIOXY-2-NITROBENZOYL]PYRROLIDINE-2-CARBOXYLATE

By carrying out the procedure as in Example 11, but replacing 4-hydroxy-1-[3,4-ethylenedioxybenzoyl]pyrrolidine-2-carboxylic acid by 4-hydroxy-N-[4,5-methlenedioxy-2-nitrobenzoyl]pyrrolidine-2-carboxylic acid, the title product is obtained.
Recrystallization solvent: isopropanol
Yield: 70%
Melting point: 166 ° C.
Spectral characteristics:
Infrared:
$\nu$OH: 3450 cm$^{-1}$
$\nu$CO: 1745 cm$^{-1}$
$\nu$CO: 1610 cm$^{-1}$
Nuclear magnetic resonance: (DMSO-d$_6$)
$\delta = 3.68$ ppm, CH$_3$
$\delta = 6.30$ ppm, O—CH$_2$—O
$\delta = 6.94$ ppm, H$_6$ (aromatics)
$\delta = 7.75$ ppm, H$_3$ (aromatics)

EXAMPLE 14: METHYL 1-(3,4-ETHYLENEDIOXYBENZOYL)-4-HYDROXYPYRROLIDINE-2-CARBOXYLATE

By carrying out the procedure as in Example 11, but replacing 4-hydroxy-1-(3,4-methylenedioxybenzoyl)-pyrrolidine-2-carboxylic acid by 1-(3,4-ethylenedioxybenzoyl)-4-hydroxypyrrolidine-2-carboxylic acid, the title product is obtained.
Recrystallization solvent: isopropanol
Yield: 60 %
Melting point: 185° C.
Spectral characteristics:
Infrared:
$\nu$OH: 3440 cm$^{-1}$
$\nu$CO: 1750 cm$^{-1}$
$\nu$CO: 1615 cm$^{-1}$
Nuclear magnetic resonance: (DMSO-d$_6$)
$\delta = 3.65$ ppm, CH$_3$
$\delta = 4.27$ ppm, O—CH$_2$CH$_2$—O
$\delta = 6.97$ ppm, aromatics

EXAMPLE 15: 1-(3,4-ETHYLENEDIOXYBENZOYL)-4-HYDROXYPYRROLIDINE-2-CARBOXAMIDE

By carrying out the procedure as in Example 9, but replacing 4-hydroxy-1-(3,4-methylenedioxybenzoyl)-pyrrolidine-2-carboxylic acid by 1-(3,4-ethylenedioxybenzoyl)-4-hydroxypyrrolidine-2-carboxylic acid, the title product is obtained.
Recrystallization solvent: water
Yield: 60%
Melting Point: 170° C.
Spectral characteristics:
Infrared:
$\nu$CO: 1690 cm$^{-1}$
Nuclear magnetic resonance: (DMSO-d$_6$)
$\delta = 4.27$ ppm, O—CH$_2$CH$_2$—O
$\delta = 6.96$ ppm, aromatics

EXAMPLE 16: ETHYL 4-HYDROXY-1-(3,4-METHYLENEDIOXYBENZOYL)PYRROLIDINE-2-CARBOXYLATE

By carrying out the procedure as in Example 11, but replacing methanol by ethanol, the title product is obtained.
Recrystallization solvent: isopropanol
Yield: 68%
Melting point: 98° C.
Spectral characteristics:
Infrared:
$\nu$OH: 3420 cm$^{-1}$
$\nu$CO: 1740, 1600 cm$^{-1}$
Nuclear magnetic resonance: (DMSO-d$_6$)
$\delta = 1.20$ ppm, CH$_3$
$\delta = 6.09$ ppm, O—CH$_2$—O
$\delta = 7.02$ ppm, aromatics

EXAMPLE 17: ETHYL 4-HYDROXY-1-(3,4-DIMETHOXYBENZOYL)-PYRROLIDINE-2-CARBOXYLATE

By carrying out the procedure as in Example 11, but replacing 4-hydroxy-1-(3,4-methylenedioxybenzoyl)-pyrrolidine-2-carboxylic acid by 4-hydroxy-1-(3,4-dimethoxybenzoyl)pyrrolidine-2-carboxylic acid and methanol by ethanol, the title product is obtained.
Recrystallization solvent: ethyl acetate
Yield: 60%
Melting point: 128° C.
Spectral characteristics:
Infrared:
$\nu$OH: 3340 cm$^{-1}$
$\nu$CO: 1740 cm$^{-1}$
$\nu$CO: 1610 cm$^{-1}$
Nuclear magnetic resonance: (DMSO-d$_6$)
$\delta = 1.20$ ppm, CH$_3$ (COOCH$_2$CH$_3$)
$\delta = 3.80$ ppm, 2 OCH$_3$
$\delta = 7.07$ ppm, aromatics

EXAMPLE 18: 4-HYDROXY-1-(4-CHLOROBENZOYL)PYRROLIDINE-2-CARBOXYLIC ACID

By carrying out the procedure as in Example 1, but replacing (4,5-methylenedioxy-2-nitro)benzoyl chloride by the 4-chlorobenzoyl chloride obtained in Preparation 8, the title product is obtained.

EXAMPLE 19: 4-HYDROXY-1-P-TOLUOYLPYRROLIDINE-2-CARBOXYLIC ACID

By carrying out the procedure as in Example 1, but replacing (4,5-methylenedioxy-2-nitro)benzoyl chloride by para-toluoyl chloride, the title product is obtained.

EXAMPLE 20: 4-HYDROXY-1-(4-TRIFLUOROMETHYLBENZOYL)PYRROLIDINE-2-CARBOXYLIC ACID

By carrying out the procedure as in Example 1, but replacing (4,5-methylenedioxy-2-nitro)benzoyl chloride by the para-trifluoromethylbenzoyl chloride obtained in Preparation 7, the title product is obtained.

EXAMPLE 21: 4-HYDROXY-1-(O-BENZYLBENZOYL)PYRROLIDINE-2-CARBOXYLIC ACID

By carrying out the procedure as in Example 1, but replacing (4,5-methylenedioxy-2-nitro)benzoyl chloride by the 2-benzylbenzoyl chloride obtained in Preparation 9, the title product is obtained.

EXAMPLE 22: 4-HYDROXY-1-(4-BENZYLOXYBENZOYL)PYRROLIDINE-2-CARBOXYLIC ACID

By carrying out the procedure as in Example 1, but replacing (4,5-methylenedioxy-2-nitro)benzoyl chloride by the 4-benzyloxybenzoyl chloride obtained in Preparation 10, the title product is obtained.

EXAMPLE 23: 4-HYDROXY-1-(3,5-DI-TERT-BUTYL-4-HYDROXYBENZOYL)-PYRROLIDINE-2-CARBOXYLIC ACID

By carrying out the procedure as in Example 1, but replacing (4,5-methylenedioxy-2-nitro) benzoyl chloride by the 3,5-di-tert-butyl-4-hydroxybenzoyl chloride obtained in Preparation 11, the title product is obtained.

EXAMPLE 24: 4-HYDROXY-1-[6-(BENZO-[1,4]-DIOXINE)CARBONYL]PYRROLIDINE-2-CARBOXYLIC ACID

By carrying out the procedure as in Example 1, but replacing 4,5-methylenedioxy-2-nitrobenzoyl chloride by the 6-(benzo-[1,4]-dioxin)carbonyl chloride obtained in Preparation 12, the title product is obtained.

EXAMPLE 25: 4-HYDROXY-1-(2,3-METHYLENEDIOXYBENZOYL)PYRROLIDINE-2-CARBOXYLIC ACID

By carrying out the procedure as in Example 1, but replacing 4,5-methylenedioxy-2-nitrobenzoyl chloride by the 2,3-methylenedioxybenzoyl chloride obtained in Preparation 13, the title product is obtained.

EXAMPLE 26: 4-HYDROXY-1-(2,3-ETHYLENEDIOXYBENZOYL)PYRROLIDINE-2-CARBOXYLIC ACID

By carrying out the procedure as in Example 1, but replacing 4,5-methylenedioxy-2-nitrobenzoyl chloride by the 2,3-methylenedioxybenzoyl chloride obtained in Preparation 14, the title product is obtained.

EXAMPLE 27: 4-HYDROXY-1-(3,4-METHYLENEDIOXYBENZOYL)PYRROLIDINE-2-N'-METHYLCARBOXAMIDE

By carrying out the procedure as in Example 9, but replacing ammonia by methylamine, the title product is obtained.

EXAMPLE 28: [4-HYDROXY-1-(3,4-METHYLENEDIOXYBENZOYL)-2-PYRROLIDINYL]MORPHOLINO KETONE 4.5 g (0.016 mol) of 4-hydroxy-1-(3,4-methylenedioxybenzoyl)pyrrolidine-2-carboxylic acid obtained in Example 6 are suspended in 110 ml of acetonitrile at 0° C. 1.1 equivalents of triethylamine are added and the reaction mixture is stirred for 30 minutes, then 1.1 equivalents of ethyl chloroformate are added while maintaining the temperature between 0° and 5° C. After stirring for 30 minutes, 1.1 equivalents of morpholine are added to the filtrate. One equivalent is stirred at room temperature for 2 hours. The precipitate is separated, the filtrate is evaporated under vacuum. The residue is recrystallized.

EXAMPLE 29: [4-HYDROXY-1-(3,4-METHYLENEDIOXYBENZOYL)-2-PYRROLIDINYL][4-(2,3,4-TRIMETHOXYBENZYL)-1-PIPERAZINYL]KETONE

By carrying out the procedure as in Example 28, but replacing morpholine by 1-(2,3,4-trimethoxybenzyl)piperazine, the title product is obtained.

EXAMPLE 30: [1-(3,4-METHYLENEDIOXYBENZOYL)-2-PYRROLIDINYL][4-(2,3,4-TRIMETHOXYBENZYL)-1-PIPERAZINYL]KETONE

By carrying out the procedure as in Example 29, but using the 1-(3,4-methylenedioxybenzoyl)pyrrolidine-2-carboxylic acid obtained in Example 5 instead of 4-hydroxy-1-(3,4-methylenedioxybenzoyl)pyrrolidine, the title product is obtained.

EXAMPLE 31: METHYL ESTER OF 4-HYDROXY-1-(4-METHYLAMINOBENZOYL)-PYRROLIDINE-2-CARBOXYLIC ACID

By carrying out the procedure as in Example 1, but replacing 4,5-methylenedioxy-2-nitrobenzoyl chloride by 4-methylaminobenzoyl chloride and trans-4-hydroxyproline by the methyl ester of trans-4-hydroxyproline, the title product is obtained.

EXAMPLE 32: 4-HYDROXY-1-(4-DIMETHYLAMINOBENZOYL)PYRROLIDINE-2-CARBOXYLIC ACID

By carrying out the procedure as in Example 1, but replacing 4,5-methylenedioxy-2-nitrobenzoyl chloride by 4-dimethylaminobenzoyl chloride, the title product is obtained.

EXAMPLE 33: 4-HYDROXY-1-(3,4-METHYLENEDIOXYBENZOYL)PYRROLIDINE-2-N'-CYCLOHEXYLCARBOXAMIDE

By carrying out the procedure as in Example 28, but replacing morpholine by cyclohexylamine, the title product is obtained. Recrystallization in ethyl acetate.
Yield: 55%
Melting point: 172° C.
Spectral characteristics:
Infrared:
OH and NH bands at 3280 cm$^{-1}$
C=O bands at 1660 and 1635 cm$^{-1}$
$^1$H Nuclear magnetic resonance (DMSO-d$_6$):
OH δ=4.95 ppm
NH δ=7.70 ppm
Percentage composition:
  Calculated: C: 63.31 H: 6.71 N: 7.77 Found: C: 63.34 H: 6.85 N: 7.60

EXAMPLE 34: 4-HYDROXY-1-(3,4-METHYLENEDIOXYBENZOYL)PYRROLIDINE-2-N'-PHENYLCARBOXAMIDE

By carrying out the procedure as in Example 28, but replacing morpholine by aniline, the title product is obtained.

EXAMPLE 35:
4-HYDROXY-1-(3,4-METHYLENEDIOXYBENZOYL)PYRROLIDINE-2-N'-BENZYLCARBOXAMIDE

By carrying out the procedure as in Example 28, but replacing morpholine by benzylamine, the title product is obtained.

EXAMPLE 36:
4-HYDROXY-1-(3,4-METHYLENEDIOXYBENZOYL)PYRROLIDINE-2-N'-(3,4,5-TRIMETHOXYPHENYL)CARBOXAMIDE

By carrying out the procedure as in Example 28, but replacing morpholine by 3,4,5-trimethoxyaniline, the title product is obtained.

EXAMPLE 37:
4-HYDROXY-1-(3,4-DIMETHOXYBENZOYL)-PYRROLIDINE-2-N'-CYCLOHEXYLCARBOXAMIDE

By carrying out the procedure as in Example 28, but replacing 4-hydroxy-1-(3,4-methylenedioxybenzoyl)-pyrrolidine-2-carboxylic acid by the 4-hydroxy-1-(3,4-dimethoxybenzoyl)pyrrolidine-2-carboxylic acid obtained in Example 4 and morpholine by cyclohexylamine, the title product is obtained. Recrystallization in an ethyl acetate/isopropanol mixture
Yield: 55%
Melting point: 208° C.
Spectral characteristics:
Infrared:
OH band at 3430 cm$^{-1}$
NH band at 3340 cm$^{-1}$
CO bands at 1660 and 1610 cm$^{-1}$
$^1$H Nuclear magnetic resonance (DMSO-d$_6$):
OCH$_3$ δ=3.80 ppm
OH δ=5.00 ppm
NH δ=7.45 ppm
Percentage composition:
   Calculated: C: 63.81 H: 7.49 N: 7.44 Found: C: 63.47 H: 7.56 N: 7.42

EXAMPLE 38:
4-HYDROXY-1-(3,4-DIMETHOXYBENZOYL)-PYRROLIDINE-2-N'-CYCLOOCTYLCARBOXAMIDE

By carrying out the procedure as in Example 37, but replacing cyclohexylamine by cyclooctylamine, the title product is obtained.
Recrystallization: ethyl acetate
Yield: 50%
Melting point: 178° C.
Spectral characteristics
Infrared:
OH band at 3440 cm$^{-1}$
NH band at 3340 cm$^{-1}$
CO bands at 1650 and 1610 cm$^{-1}$
$^1$H Nuclear magnetic resonance (DMSO-d$_6$):
CH$_2$ (cyclooctyl) δ=1.5 ppm
OCH$_3$ δ=3.8 ppm
OH δ=4.95 ppm
NH δ=7.80 ppm
Percentage composition:
   Calculated: C: 63.32 H: 7.97 N: 6.92 Found: C: 63.74 H: 7.60 N: 6.63

EXAMPLE 39:
4-HYDROXY-1-(3,4-DIMETHOXYBENZOYL)-PYRROLIDINE-2-N'-CYCLOPROPYLCARBOXAMIDE

By carrying out the procedure as in Example 37, but replacing cyclohexylamine with cyclopropylamine, the title product is obtained.
Recrystallization: ethyl acetate
Yield: 42%
Melting point: 208° C.
Spectral characteristics:
Infrared:
OH band at 3440 cm$^{-1}$
NH band at 3340 cm$^{-1}$
CO bands at 1650 and 1610 cm$^{-1}$
$^1$H Nuclear magnetic resonance (DMSO-d$_6$):
CH (cyclopropyl) δ=2.60 ppm
OCH$_3$ δ=3.8 ppm
OH δ=4.95 ppm
NH δ=8.00 ppm
Percentage composition:
   Calculated C: 61.06 H: 6.63 N: 8.37 Found: C: 60.67 H: 6.59 N: 8.06

EXAMPLE 40:
4-HYDROXY-1-(3,4-METHYLENEDIOXYBENZOYL)PYRROLIDINE-2-N'-CYCLOOCTYLCARBOXAMIDE

By carrying out the procedure as in Example 28, but replacing morpholine by cyclooctylamine, the title product is obtained.
Recrystallization: ethyl acetate
Yield: 50%
Melting point: 188° C.
Spectral characteristics:
Infrared:
OH bands and NH bands at 3290 cm$^{-1}$
CO bands at 1670 and 1630 cm$^{-1}$
$^1$H Nuclear magnetic resonance (DMSO-d$_6$):
OH δ=4.95 ppm
NH δ=7.75 ppm
Percentage composition:
   Calculated: C: 64.93 H: 7.26 N: 7.21 Found C: 64.40 H: 7.39 N: 7.19

EXAMPLE 41:
4-HYDROXY-1-(3,4-METHYLENEDIOXYBENZOYL)PYRROLIDINE-2-N'-CYCLOPROPYLCARBOXAMIDE

By carrying out the procedure as in Example 28, but replacing morpholine by cyclopropylamine, the title product is obtained.
Recrystallization: ethyl acetate
Yield: 52%
Melting point: 180° C.
Spectral characteristics:
Infrared:
OH bands at 3330 cm$^{-1}$
NH bands at 3280 cm$^{-1}$
CO bands at 1680 cm$^{-1}$
$^1$H Nuclear magnetic resonance (DMSO-d$_6$):
CH (cyclopropyl) δ=2.60 ppm
OH δ=5.00 ppm
NH δ=8.00 ppm
Percentage composition:
   Calculated: C: 60.37 H: 5.69 N: 8.80 Found: C: 59.97 H: 5.84 N: 8.48

EXAMPLE 42:
4-HYDROXY-1-(3,4-METHYLENEDIOXYBEN-ZOYL)PYRROLIDINE-2-N'-CYCLOHEXYLMETHYLCARBOXAMIDE

By carrying out the procedure as in Example 28, but replacing morpholine by cyclohexylmethylamine, the title product is obtained.
Recrystallization: ethyl acetate
Yield: 46%
Melting point: 178° C.
Spectral characteristics:
Infrared:
OH bands and NH bands at 3290 cm$^{-1}$
CO bands at 1670 and 1650 cm$^{-1}$
$^1$H Nuclear magnetic resonance (DMSO-d$_6$):
CH$_2$ (NHC$\underline{H}_2$ cyclohexyl) δ=2.90 ppm
OH δ=4.95 ppm
NH δ=7.85 ppm
Percentage composition:
  Calculated: C: 64.15 H: 6.99 N: 7.48 Found: C: 64.39 H: 6.97 N: 7.48

EXAMPLE 43:
4-HYDROXY-1-(3,4-DIMETHOXYBENZOYL)-PYRROLIDINE-2-N'-(CYCLOHEXYLMETHYL)-CARBOXAMIDE

By carrying out the procedure as in Example 37, but replacing cyclohexylamine by cyclohexylmethylamine, the title product is obtained.
Yield: 45%
Melting point: 158° C.
Spectral characteristics:
Infrared:
OH band and NH band at 3290 cm$^{-1}$
CO band at 1660 cm$^{-1}$
$^1$H Nuclear magnetic resonance (DMSO-d$_6$):
CH$_2$ (NH—C$\underline{H}_2$ cyclohexyl)δ=2.90 ppm
OCH$_3$ δ=3.8 ppm
OH δ=4.95 ppm
NH δ=7.85 ppm
Percentage composition:
  Calculated: C: 64.59 H: 7.74 N: 7.17 Found: C: 64.15 H: 7.69 N: 6.98

EXAMPLE 44:
4-HYDROXY-1-(3,4,5-TRIMETHOXYBENZOYL)-PYRROLIDINE-2-N'-(CYCLOHEXYLMETHYL)-CARBOXAMIDE

By carrying out the procedure as in Example 42, but replacing 4-hydroxy-1-(3,4-methylenedioxybenzoyl)-pyrrolidine-2-carboxylic acid by the 4-hydroxy-1-(3,4,5-trimethoxybenzoyl)pyrrolidine-2-carboxylic acid described in Example 8, the title product is obtained.
Recrystallization: ethyl acetate
Yield: 77%
Melting point: 152° C.
Spectral characteristics:
Infrared:
OH bands at 3300 cm$^{-1}$
C=O bands at 1665 and 1630 cm$^{-1}$
$^1$H Nuclear magnetic resonance (DMSO-d$_6$):
CH$_2$ (NHC$\underline{H}_2$ cyclohexyl) δ=2.90 ppm
OCH$_3$δ=3.80 ppm
OH δ=4.95 ppm
NH δ=7.90 ppm
Percentage composition:
  Calculated C: 62.83 H: 7.67 N: 6.66 Found C: 63.21 H: 7.79 N: 6.42

EXAMPLE 45:
4-HYDROXY-1-(3,4-METHYLENEDIOXYBEN-ZOYL)PYRROLIDINE-2-[3-(di-N',N'-DIMETHYLAMINO)PROPYL CARBOXYLATE](OXALATE)

In 2 125-ml furnaces each containing 30 ml of 1-propanol, 1 equivalent (0.007 mol) of sodium is added. After stirring for one hour, 2 g (0.007 mol) of 4-hydroxy-1-(3,4-methylenedioxybenzoyl)pyrrolidine-2-carboxylic acid (Example 6) are added to one of them and 1 equivalent of N-(3-chloropropyl)-N,N-dimethylamine (hydrochloride) to the other.

The stirring is continued for 1 hour. The mixture containing the aminopropyl compound is poured dropwise into the first mixture obtained. This reaction mixture is then refluxed for 4 hours. The 1-propanol is then removed under reduced pressure. The residual oil is taken up by 50 ml of water and then this aqueous phase is extracted 3 times with 50 ml of ethyl acetate. The organic phases are combined, dried over magnesium sulfate and removed under vacuum.

An oil is obtained to which 5 ml of propanol are added; to the solution thus obtained, one equivalent of oxalic acid is added. The reaction mixture is refluxed for 30 minutes and then after cooling, it is poured into 200 ml of ethyl ether; after stirring, the oxalate is filtered.
Recrystallization: acetonitrile
Yield: 61%
Melting point: 120° C.
Spectral characteristics:
Infrared:
OH band at 3360 cm$^{-1}$
C=O bands at 1730 and 1630 cm$^{-1}$
$^1$H Nuclear magnetic resonance (DMSO-d$_6$):
2CH$_3$ δ=2.70 ppm
3CH$_2$ propyl δ=1.95; 3.00 and 4.15 ppm
Percentage composition:
  Calculated: C: 52.86 H: 5.76 N: 6.16 Found: C: 53.08 H: 5.81 N: 5.84

EXAMPLE 46:
4-HYDROXY-(3,4-METHYLENEDIOXYBEN-ZOYL)PYRROLIDINE-2-[2-(N', N'-DIMETHYLAMINO)ETHYL CARBOXYLATE]OXALATE

By carrying out the procedure as in Example 45, but replacing N-(3-chloropropyl)-N,N-dimethylamine (hydrochloride) by N-(2-chloroethyl)-N,N-dimethylamine (hydrochloride), the title product is obtained.
Recrystallization: acetonitrile/ethyl ether
Yield: 40%
Melting point: 128° C.
Spectral characteristics:
Infrared:
OH bands: 3400 cm$^{-1}$
C=O bands: 1750, 1720 and 1630 cm$^{-1}$
$^1$H Nuclear magnetic resonance (DMSO-d$_6$):
2CH$_3$ δ=2.80 ppm
2CH$_2$ (ethyl) δ=3.30 and 4.40 ppm
OH δ=5.05 ppm
Percentage composition:
  Calculated C: 51.81 H: 5.49 N: 6.36 Found: C: 51.47 H: 5.36 N: 5.92

EXAMPLE 47: 4-HYDROXY-1-(3,4-METHYLENEDIOXYBENZOYL)PYRROLIDINE-2-(2-MORPHOLINOETHYL CARBOXYLATE)(OXALATE)

By carrying out the procedure as in Example 45, but replacing N-(3-chloropropyl)-N,N-dimethylamine (hydrochloride) by N-(2-chloroethyl)morpholine (hydrochloride), the title product is obtained.
Recrystallization: acetonitrile
Yield: 86%
Melting point: 128° C.
Spectral characteristics:
Infrared:
OH bands at 3370 cm$^{-1}$
CO bands at 1745 and 1630 cm$^{-1}$
$^1$H Nuclear magnetic resonance (DMSO-d$_6$):
4CH$_2$ (morpholine) $\delta=2.8$ and 3.6 ppm
Percentage composition:
Calculated: C: 52.88 H: 5.43 N: 5.80 Found: C: 52.42 H: 5.44 N: 6.25

EXAMPLE 48: 4-HYDROXY-1-(3,4-DIMETHOXYBENZOYL)-PYRROLIDINE-2-(2-MORPHOLINOETHYL CARBOXYLATE)(OXALATE)

By carrying out the procedure as in Example 47, but replacing 4-hydroxy-1-(3,4-methylenedioxybenzoyl)-pyrrolidine-2-carboxylic acid by the 4-hydroxy-1-(3,4-dimethoxybenzoyl)pyrrolidine-2-carboxylic acid obtained in Example 4, the title product is obtained.
Recrystallization: acetonitrile
Yield: 40%
Melting point: 150° C.
Spectral characteristics:
Infrared:
OH band at 3460 cm$^{-1}$
$^1$H Nuclear magnetic resonance (DMSO-d$_6$):
4CH$_2$ (morpholine) $\delta=2.7$ and 3.6 ppm
OCH$_3$ $\delta=3.80$ ppm

EXAMPLE 49: 4-HYDROXY-1-(3,4-METHYLENEDIOXYBENZOYL)PYRROLIDINE-2-(2-PIPERIDINOETHYL CARBOXYLATE) (OXALATE)

By carrying out the procedure as in Example 45, but replacing N-(3-chloropropyl)-N,N-dimethylamine hydrochloride by N-2-chloroethylpiperidine (hydrochloride), the title product is obtained.
Recrystallization: acetonitrile
Yield: 80%
Melting point: 128° C.
Spectral characteristics:
Infrared:
OH bands at 3460 cm$^{-1}$
CO bands at 1745 and 1630 cm$^{-1}$
$^1$H Nuclear magnetic resonance (DMSO-d$_6$):
4CH$_2$ (piperidine) $\delta=2.00$ and 3.05 ppm
Percentage composition:
Calculated: C: 54.99 H: 5.87 N: 5.83 Found C: 54.91 H: 5.90 N: 6.24

EXAMPLE 50: 4-HYDROXY-1-(3,4-METHYLENEDIOXYBENZOYL)PYRROLIDINE-2-[3-(N,N-DIETHYLAMINO)PROPYL CARBOXYLATE](OXALATE)

By carrying out the procedure as in Example 45, but replacing N-(3-chloropropyl)-N,N-dimethylamine (hydrochloride) by N-(3-chloropropyl)-N,N-diethylamine (hydrochloride), the title product is obtained.
Recrystallization: ethyl ether
Yield: 64%
Melting point: 130° C.
Spectral characteristics:
Infrared:
CO bands at 1740 and 1625 cm$^{-1}$
$^1$H Nuclear magnetic resonance (DMSO-d$_6$):
2CH$_3$ (ethyl) $\delta=0.9$ ppm
2CH$_2$ (ethyl) $\delta=2.40$ ppm
OH $\delta=5.10$ ppm

EXAMPLE 51: 4-HYDROXY-1-(3,4-DIMETHOXYBENZOYL)-PYRROLIDINE-2-N',N'-DIETHYLCARBOXAMIDE 4 g (0.013 mol) of 4-hydroxy-1-(3,4-dimethoxybenzoyl)pyrrolidine-2-carboxylic acid (obtained in Example 4) are suspended in 100 ml of acetonitrile at 0° C. 1.1 equivalents of triethylamine are added. After stirring for 20 minutes, 1.1 equivalents of ethyl chloroformate are added while maintaining the temperature between 0° and 5° C. The reaction mixture is stirred for 20 minutes and then 1.1 equivalents of diethylamine are added. This mixture is then stirred at room temperature for 2 hours. The acetonitrile is evaporated under vacuum, the residual oil is taken up in 100 ml of water and then this aqueous phase is extracted with 3 times 100 ml of ethyl acetate. These organic phases are combined, dried and removed under vacuum. The oil obtained crystallizes after addition of ethyl ether. It is recrystallized in ethyl acetate
Yield: 50%
Melting point: 152° C.
Spectral characteristics:
Infrared:
OH band at 3440 cm$^{-1}$
CO band at 1645 and 1610 cm$^{-1}$
$^1$H Nuclear magnetic resonance (DMSO-d$_6$):
2(NCH$_2$CH$_3$): 1.00 and 1.25 ppm
OCH$_3$ $\delta=3.80$ ppm
2(N-CH$_2$CH$_3$): 3.18 and 3.50 ppm
Percentage composition:
Calculated: C: 61.59 H: 7.47 N: 7.99 Found: C: 61.74 H: 7.36 N: 7.83

EXAMPLE 52: 1-(3,4-DIMETHOXYBENZOYL)PYRROLIDINE-2,4-CARBOLACTONE

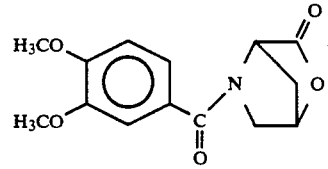

Using the same process as that described in the preceding example, but replacing diethylamine by imidazole, the title product is obtained.
Yield: 32%
Melting point: 132° C.
Spectral characteristics:
Infrared:
CO bands at 1800 and 1630 cm$^{-1}$
$^1$H Nuclear magnetic resonance (DMSO-d$_6$):
OCH$_3$ $\delta=3.80$ ppm Percentage composition:
Calculated: C: 60.64 H: 5.45 N: 5.05 Found: C: 60.46 H: 5.48 N: 4.92

EXAMPLE 53:
4-HYDROXY-1-(3,4-METHYLENEDIOXYBENZOYL)PYRROLIDINE-2-N,N'-DIMETHYLCARBOXAMIDE

By carrying out the procedure as in Example 51, but replacing 4-hydroxy-1-(3,4-dimethoxybenzoyl)pyrrolidine-2-carboxylic acid by 4-hydroxy-1-(3,4-methylenedioxybenzoyl)pyrrolidine-2-carboxylic acid (obtained in Example 6) and N,N-diethylamine by N,N-dimethylamine, the title product is obtained.
Yield: 50%
Melting point: 170° C.
Spectral characteristics:
Infrared:
OH band at 3450 cm$^{-1}$
CO band at 1640 cm$^{-1}$
$^1$H Nuclear magnetic resonance (DMSO-d$_6$):
2C$\underline{H}_3$: 3.10 and 2.83 ppm
O—C$\underline{H}_2$—O 6.08 ppm

EXAMPLE 54:
4-HYDROXY-1-(3,4,5-TRIMETHOXYBENZOYL)-PYRROLIDINE-2-CARBOXAMIDE

By carrying out the procedure as in Example 9, but replacing 4-hydroxy-1-(3,4-methylenedioxybenzoyl)-pyrrolidine-2-carboxylic acid by the 4-hydroxy-1-(3,4,5-trimethoxybenzoyl)pyrrolidine-2-carboxylic acid obtained in Example 8, the title product is obtained.
Yield: 60%
Melting point: 172 ° C.
Spectral characteristics:
Infrared:
CO band at 1665 and 1620 cm$^{-1}$
$^1$H Nuclear magnetic resonance (DMSO-d$_6$):
3OC$\underline{H}_3$ 3.8 ppm
O$\underline{H}$ 4.96 ppm
Percentage composition:
Calculated: C: 55.54 H: 6.21 N: 8.63 Found: C: 55.28 H: 5.99 N: 8.03

EXAMPLE 55:
ETHYL4-HYDROXY-1-(3,4-ETHYLENEDIOXYBENZOYL)PYRROLIDINE-2-CARBOXYLATE

By carrying out the procedure as in Example 11, but replacing: -4-hydroxy-1-(3,4-methylenedioxybenzoyl)-pyrrolidine-2-carboxylic acid by the 4-hydroxy-1-(3,4-ethylenedioxybenzoyl)pyrrolidine-2-carboxylic acid obtained in Example 10, —methanol by ethanol, the title product is obtained.
Recrystallization: ethyl acetate
Yield: 70%
Melting point: 108° C.
Spectral characteristics:
Infrared:
OH bands: 3420 cm$^{-1}$
CO bands: 1740, 1610 cm$^{-1}$
$^1$H Nuclear magnetic resonance (DMSO-d$_6$)
COOC$\underline{H}_2$C$\underline{H}_3$: 1.19 ppm
OC$\underline{H}_2$C$\underline{H}_2$O: 4.28 ppm
COOC$\underline{H}_2$C$\underline{H}_3$: 4.13 ppm
OH: 5.12 ppm
Percentage composition:
Calculated: C: 59.80 H: 5.95 N: 4.35 Found: C: 59.81 H: 5.80 N: 4.31

EXAMPLE 56:
METHYL4-HYDROXY-1-(3,4,5-TRIMETHOXYBENZOYL)PYRROLIDINE-2-CARBOXYLATE

By carrying out the procedure as in Example 11, but replacing 4-hydroxy-1-(3,4-methylenedioxybenzoyl)-pyrrolidine-2-carboxylic acid by the 4-hydroxy-1-(3,4,5-trimethoxybenzoyl)pyrrolidine-2-carboxylic acid obtained in Example 8, the title product is obtained.
Recrystallization: ethyl acetate
Yield: 40%
Melting point: 126° C.
Spectral characteristics:
Infrared:
OH band: 3485 cm$^{-1}$
CO band: 1730 cm$^{-1}$
$^1$H Nuclear magnetic resonance (DMSO-d$_6$):
COOC$\underline{H}_3$: 3.66 ppm
3OC$\underline{H}_3$: 3.80 ppm
OH: 5.10 ppm
Percentage composition:
Calculated: C: 56.63 H: 6.23 N: 4.12 Found: C: 55.08 H: 6.24 N: 3.95

EXAMPLE 57:
4-HYDROXY-1-(4-METHOXYBENZOYL)PYRROLIDINE-2-CARBOXYLIC ACID

By carrying out the procedure as in Example 1, but replacing 4,5-methylenedioxy-2-nitrobenzoyl chloride by the 4-methoxybenzoyl chloride obtained in Preparation 15, the title product is obtained.
Yield: 50%
Melting Point: 192° C.
Spectral characteristics:
Infrared:
OH band: 3500, 2940 cm$^{-1}$
CO band: 1740 cm$^{-1}$
$^1$H Nuclear magnetic resonance (DMSO-d$_6$):
OC$\underline{H}_3$: 3.80 ppm
CHO$\underline{H}$: 5.03 ppm
COO$\underline{H}$: 12.71 ppm
Percentage composition:
Calculated: C: 58.86 H: 5.69 N: 5.28 Found: C: 58.80 H: 5.69 N: 5.24

EXAMPLE 58: METHYL 4-HYDROXY-1-(4-METHOXYBENZOYL)PYRROLIDINE-2-CARBOXYLATE

By carrying out the procedure as in Example 11, but replacing 4-hydroxy-1-(3,4-methylenedioxybenzoyl)-pyrrolidine-2-carboxylic acid by the 4-hydroxy-1-(4-methoxy-benzoyl)pyrrolidine-2-carboxylic acid obtained in Example 57, the title product is obtained.
Recrystallization: ethyl ether
Yield: 40%
Melting point: 92° C.
Spectral characteristics:
Infrared:
OH band: 3480 cm$^{-1}$
CO band: 1740, 1605 cm$^{-1}$
$^1$H Nuclear magnetic resonance (DMSO-d$_6$):
COOC$\underline{H}_3$: 3.65 ppm
OH: 5.11 ppm
Percentage composition:
Calculated: C: 60.20 H: 6.13 N: 5.01 Found: C: 60.10 H: 5.98 N: 4.96

EXAMPLE 59: ETHYL 4-HYDROXY-1-(3,4,5-TRIMETHOXBENZOYL)PYRROLIDINE-2-CARBOXYLATE

By carrying out the procedure as in Example 56, but replacing methanol by ethanol, the title product is obtained.
Recrystallization: ethyl ether
Yield: 70%
Melting point: 78° C.
Spectral characteristics:
Infrared:
OH bands: 3480 cm$^{-1}$
CO bands: 1720 cm$^{-1}$
$^1$H Nuclear magnetic resonance (DMSOD$_6$):
COO$\underline{CH_2}$CH$_3$: 1.19 ppm
COOCH$_2$—$\underline{CH_3}$: 4.11 ppm
OH: 5.11 ppm

EXAMPLE 60: ETHYL 4-HYDROXY-1-(4-METHOXYBENZOYL)PYRROLIDINE-2-CARBOXYLATE

By carrying out the procedure as in Example 58, but replacing methanol by ethanol, the title product is obtained.
Recrystallization: ethyl ether/petroleum ether
Yield: 50%
Melting point: 64° C.
Spectral characteristics:
Infrared:
OH bands: 3360 cm$^{-1}$
CO bands: 1745, 1610 cm$^{-1}$
$^1$H Nuclear magnetic resonance (DMSOD$_6$):
COOCH$\underline{C_2CH_3}$: 1.19 ppm
OCH$_3$: 3.80 ppm
COO$\underline{CH_2}$CH$_3$: 4.11 ppm
OH: 5.11 ppm
Percentage composition:
Calculated: C: 61.42 H: 6.42 N: 4.77 Found: C: 61.08 H: 6.35 N: 4.76

EXAMPLE 61: ETHYL 1-(4,5-METHYLENEDIOXY-2-NITROBENZOYL)-PYRROLIDINE-2-CARBOXYLATE

By carrying out the procedure as in Example 11, but replacing 4-hydroxy-1-(3,4-methylenedioxybenzoyl)-pyrrolidine-2-carboxylic acid by 1-(4,5-methylenedioxy-2-nitrobenzoyl)pyrrolidine-2-carboxylic acid and methanol by ethanol, the title product is obtained.
Recrystallization: ethyl ether
Yield: 85%
Melting point: 94° C.
Spectral characteristics:
Infrared:
CO bands: 1740 and 1630 cm$^{-1}$
NO$_2$ bands: 1515 and 1330 cm$^{-1}$
$^1$H Nuclear magnetic resonance (DMSOD$_6$):
COOCH$_2$CH$_3$: 1.22 ppm
COO$\underline{CH_2}$CH$_3$: 4.14 ppm
CH: 4.42 ppm
O—CH$_2$—O: 6.30 ppm
Percentage composition:
Calculated: C: 53.57 H: 4.79 N: 8.32 Found: C: 53.74 H: 4.70 N: 8.45

EXAMPLE 62: [4-HYDROXY-1-(3,4-DIMETHOXYBENZOYL)-2-PYRROLIDINE][4-(2,3,4-TRIMETHOXYBENZYL-1-PIPERAZINYL]KETONE

By carrying out the procedure as in Example 29, but replacing 4-hydroxy-1-(3,4-methylenedioxybenzoyl)-pyrrolidine-2-carboxylic acid by 4-hydroxy-1-(3,4-dimethoxybenzoyl)pyrrolidine-2-carboxylic acid, the title product is obtained.

PHARMACOLOGICAL STUDY OF THE PRODUCTS OF THE INVENTION

EXAMPLE 63: STUDY OF ACUTE TOXICITY

Acute toxicity was determined after intraperitoneal administration of the products of the invention to groups of male mice of about 25 g. The animals were observed at regular intervals for the first hours following the administration and then daily during the week following the administration.

The compounds of the invention are not very toxic as none of them has an LD$_{50}$ (lethal dose 50 which causes the death of half of the animals treated) lower than 500 mg.kg$^{-1}$.

EXAMPLE 64: AMNESIA INDUCED BY SCOPOLAMINE

Scopolamine (1 mg.kg$^{-1}$ ip) is injected 30 minutes and the test products 60 minutes before the beginning of the training test. The apparatus used comprises two compartments: one illuminated and the other dark and possessing an electrified floor. The mouse is introduced in the illuminated compartment, when it enters the dark compartment, it receives a weak electric shock. After training 24 hours earlier, the test consists in measuring the latent period between two entries into the dark compartment. Compared to an untreated animal, scopolamine reduces this time at a dose of 0.03 mg.kg$^{-1}$.

The compounds of the invention antagonize the amnesia induced by scopolamine by increasing this delay by about 75%.

EXAMPLE 65: PHARMACEUTICAL COMPOSITION: TABLET

Tablets containing a dose of 10 mg of Trans (L)1-(3,4-dimethoxybenzoyl)-4-hydroxypyrrolidine-2-N',N'-diethyl-carboxamide.
Preparation formula for 1000 tablets.

| | |
|---|---|
| Trans(L)1-(3,4-Dimethoxybenzoyl)-4-hydroxypyrrolidine-2-N',N'-diethylcarboxamide | 10 g |
| Wheat starch | 10 g |
| Maize starch | 10 g |
| Lactose | 60 g |
| Magnesium stearate | 2 g |
| Silica | 1 g |
| Hydroxypropyl cellulose | 2 g |

We claim:
1. A compound selected from those of formula (I):

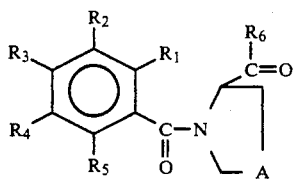

(I)

wherein

A represents a CHOH,

R₁, R₂, R₃, R₄, R₅, which are identical or different, represent independently of one another a hydrogen, lower-alkyl, or hydroxyl, lower alkoxy group, or alternatively two adjacent groups selected from R₁, R₂, R₃, R₄, R₅, namely R₁ and R₂, or R₂ and R₃ or R₃ and R₄ or R₄, and R₅ together form an —O—CH₂—O, —O—CH₂— CH₂—O— bridge, it being understood that:

R₁, R₂, R₃, R₄, R₅ cannot simultaneously represent hydrogen,

R₆ represents hydroxyl or lower alkoxy, amino, NR₇R₈, or —O—B—NR₇R₈ group with B representing lower alkyl and R₇, R₈, which are identical or different, represent hydrogen lower alkyl, cycloalkyl, cycloalkyl(lower alkyl), phenyl, lower phenylalkyl, substituted phenyl, or substituted lower phenylalkyl or R₇ and R₈ form with the nitrogen which carries them a monocyclic or bicyclic heterocyclic system, each ring comprising five or six atoms and optionally integrating in its skeleton one or two hetero atoms chosen from nitrogen, oxygen, and sulfur, and optionally substituted by lower alkyl, phenyl, lower phenylalkyl, substituted lower phenylalkyl, or substituted phenyl, the term substituted phenylalkyl, meaning that the aromatic nucleus of the group may be substituted by one or more lower alkyl, lower alkoxy, or trifluoromethyl groups, it being understood that cycloalkyl means a group with 3 to 8 carbon atoms inclusive and that lower alkyl means a linear or branched group with 1 to 6 carbon atoms inclusive, as well as, when appropriate, their isomers and their addition salts with a pharmaceutically, acceptable acid or base.

2. A compound as claimed in claim 1, in which A represents CHOH, its trans-(L) or (2S, 4R), trans-(D) or (2R, 4S), cis-(L) or (2S, 4S) or cis-(D) or (2R, 4R) isomers as well as, where appropriate, its addition salts with a pharmaceutically, acceptable acid or base.

3. A compound as claimed in claim 1, in which A represents CHOH having the trans-(L) or (2S, 4R) configuration and, where appropriate, its addition salts with a pharmaceutically, acceptable acid or base.

4. A compound as claimed in claim 1, in which R₂, R₃, R₄, which are identical or different, represent lower alkoxy or hydrogen or hydroxyl whereas R₁ and R₅ each represent hydrogen group, its isomers as well as its addition salts with a pharmaceutically, acceptable acid or base.

5. A compound as claimed in claim 1, in which R₆ represents hydroxyl, lower alkoxy, amino, lower N,N-dialkylamino, or 4-(2,3,4-trimethoxybenzyl)-1-piperazinyl, its isomers as well as, where appropriate, its addition salts with a pharmaceutically, acceptable acid or base.

6. A compound as claimed in claim 1, which is selected from trans-L-1-(3,4-dimethoxybenzoyl)-4-hydroxypyrrolidine-2-N',N'-diethyl carboxamide, the corresponding carboxylic acid, their trans-(D), cis-(L) and cis-(D) isomers, as well as their addition salts with a pharmaceutically, acceptable base.

7. A compound as claimed in claim 1, which is selected from trans-L-1-(3,4,5-trimethoxybenzoyl)-4-hydroxypyrrolidine-2-carboxylic acid, its trans-(D), cis-(L) and cis-(D) isomers, as well as its addition salts with a pharmaceutically, acceptable base.

8. A compound as claimed in claim 1, which is selected from trans-L-1-(3,4-dimethoxybenzoyl)-4-hydroxypyrrolidine-2-N'-(cyclohexylmethyl)carboxamide, and its trans-(D), cis-(L) cis-(D) isomers.

9. A compound as claimed in claim 1, which is trans-L-1-(3,4-dimethoxybenzoyl)-4-hydroxypyrrolidine-2-N'-cyclopropylcarboxamide, its trans-(D), cis-(L) and cis-(D) isomers.

10. A compound as claimed in claim 1 which is selected from trans-L-1-(3,4-methylenedioxybenzoyl)-4-hydroxypyrrolidine-2-N'(cyclohexylmethyl)carboxamide, and its trans-(D), cis-(L) and cis-(D) isomers.

11. A compound as claimed in claim 1, which is selected from 3-(N',N'-dimethylamino)propyl trans-L-1-(3,4-methylene-dioxybenzoyl)-4-hydroxypyrrolidine-2-carboxylate, its trans-(D), cis-(L) and cis-(D) isomers, as well as its addition salts with a pharmaceutically, acceptable acid.

12. A compound as claimed in claim 1, which is selected from 2-morpholinoethyl trans-L-1-(3,4-methylenedioxybenzoyl)-4-hydroxypyrrolidine-2-carboxylate, its trans-(D), cis-(L) and cis-(D) isomers, as well as its addition salts with a pharmaceutically, acceptable acid.

13. A compound as claimed in claim 1, which is selected from 2-morpholinoethyl trans-L-1-(3,4-dimethoxybenzoyl)-4-hydroxypyrrolidine-2-carboxylate, its trans-(D), cis-(L) and cis-(D) isomers, as well as its addition salts with a pharmaceutically, acceptable acid.

14. A compound as claimed in claim 1, which is selected from trans-L-[4-hydroxy-1-(3,4-methylenedioxybenzoyl)-2-pyrrolidinyl][4-(2,3,4-trimethoxybenzyl)-1-piperazinyl]ketone, its trans-(D), cis-(L) and cis-(D) isomers, as well as its addition salts with a pharmaceutically, acceptable acid.

15. A compound as claimed in claim 1, which is selected from trans-L-[4-hydroxy-1-(3,4-dimethoxybenzoyl)-2-pyrrolidinyl][4-(2,3,4-trimethoxybenzyl)-1-piperazinyl]ketone, its trans-(D), cis-(L) and cis-(D) isomers, as well as its addition salts with a pharmaceutically, acceptable acid.

16. A compound as claimed in claim 1, in which R₆ represents a lower alkoxy group, as well as its isomers.

17. A compound as claimed in claim 1, which is selected from trans-L-1-(3,4,5-trimethoxybenzoyl)-4-hydroxypyrrolidine-2-N'-cyclohexylmethylcarboxamide, its trans-(D), cis-(L) and its cis-(D) isomers.

18. A compound as claimed in claim 1, which is selected from trans-L-1-(3,4-dimethoxybenzoyl)-4-hydroxypyrrolidine-2N'-cyclooctylcarboxamide, and its trans-(D), cis-(L) and cis-(D) isomers.

19. A compound as claimed in claim 1, which is selected from trans-L-1-(3,4-dimethoxybenzoyl)-4-hydroxypyrrolidine-2-carboxamide, and its trans-(D), cis-(L) and cis-(D) isomers.

20. A compound as claimed in claim 1, which is selected from ethyl trans-L-1-(3,4,5-trimethoxybenzoyl)-

4-hydroxy-pyrrolidine-2-carboxylate, and its trans-(D), cis-(L) and cis-(D) isomers.

21. A pharmaceutical composition suitable for use in the treatment of a living animal afflicted with a condition resulting from ischemia or hypoxic or oxygen deficiency disorders, containing as active ingredient an amount of a compound as claimed in claim 1 which is effective for such purpose in combination with one or more pharmaceutically-acceptable excipients or vehicles.

22. A method for treating a living animal afflicted with a condition resulting from ischemia or hypoxic or oxygen defiency disorders consisting essentially of the step of administering to the said living animal an amount of a compound of claim 1 which is effective for alleviation of the said condition.

23. A compound as claimed in claim 1, which is 4-hydroxy-1-(3,5-di-tert-butyl-4-hydroxybenzoyl)-pyrrolidine-2-carboxylic acid.

* * * * *

UNITED STATES PATENT AND TRADEMARK OFFICE
CERTIFICATE OF CORRECTION

PATENT NO. : 5,332,735
DATED : July 26, 1994 Page 1 of 3
INVENTOR(S) : Sylvain Rault, Marie P. Foloppe, Max Robba, Michel Boulouard, Pierre Renard, Michelle Devissaguet, Gérard Adam It is certified that error appears in the above-indentified patent and that said Letters Patent is hereby corrected as shown below:

TITLE PAGE "BENZOYLPYROLINE" should read -- BENZOYLPROLINE --
Column 1, line 1; "BENZOYLPYROLINE" should read
    -- BENZOYLPROLINE --
Column 1, line 59; " —CH- " should read -- —$CH_2$- --
Column 1, line 60; delete the " $_2$ " (first occurrence)
Column 1, line 66; " —CH- " should read -- —$CH_2$- --
Column 1, line 67; delete the -- $_2$ -- (first occurrence)
Column 12, line 20; delete the " 8 " at the end of the line.
Column 12, line 21; insert " [ " at the beginning of the line.
    before "3,4"
Column 24, line 2; insert a space between " METHYL " and " 4 "
Column 25, line 1; insert a space between " ETHYL " and " 4 "
Column 27, line 11; ( line 2 after the formula) delete
    the " a " (after represents)
Column 27, line 13; delete " of one another a "
Column 27, line 14; delete the word " group "

Column 27, line 16; insert a comma after " $R_3$ "
    (second occurrence)
Column 27, line 17; insert a comma after " $R_4$ "(first occurrence)
    and " $R_5$ "

Column 27, line 23; delete the word " group "
Column 27, line 37; delete the word " phenylalkyl, "

Colunm 27, line 46; delete the comma after " pharmaceutically "
    and insert a hyphen.
Column 27, line 52; delete the comma after " pharmaceutically "
    and insert a hyphen.
Column 27, line 56; delete the comma after "pharmaceutically "
    and insert a hyphen.

UNITED STATES PATENT AND TRADEMARK OFFICE
CERTIFICATE OF CORRECTION

PATENT NO. : 5,332,735

DATED : July 26, 1994

Page 2 of 3

INVENTOR(S) : Sylvain Rault, Marie P. Foloppe, Max Robba, Michel Boulouard, Pierre Renard, Michelle Devissaguet, Gérard Adam It is certified that error appears in the above-indentified patent and that said Letters Patent is hereby corrected as shown below:

```
Column 27, line 60; delete the word " group "
Column 27, line 61; delete the comma after " pharmaceutically "
     and insert a hyphen.
Column 27, line 67; delete the comma after " pharmaceutically "
     and insert a hyphen.
Column 28, line  6; delete the comma after " pharmaceutically "
     and insert a hyphen.
Column 28, line 11; delete the comma after " pharmaceutically "
     and insert a hyphen.
Column 28, line 16; insert -- selected from -- after the word
     " is "
Column 28, line 18; insert -- and -- before the word " its "
Column 28, line 28; delete the comma after " pharmaceutically "
     and insert a hyphen.
Column 28, line 34; delete the comma after " pharmaceutically "
     and insert a hyphen.
Column 28, line 40; delete the comma after " pharmaceutically "
     and insert a hyphen.
Column 28, line 46; delete the comma after " pharmaceutically "
     and insert a hyphen.
Column 28, line 52; delete the comma after " pharmaceutically "
     and insert a hyphen.
```

UNITED STATES PATENT AND TRADEMARK OFFICE
CERTIFICATE OF CORRECTION

PATENT NO. : 5,332,735

DATED : July 26, 1994

INVENTOR(S) : Sylvain Rault, Marie P. Foloppe, Max Robba, Michel Boulouard, Pierre Renard, Michelle Devissaguet, Gérard Adam It is certified that error appears in the above-indentified patent and that said Letters Patent is hereby corrected as shown below:

Column 28, line 58; insert -- and -- before the word " its " (first occurrence)

Signed and Sealed this

Seventeenth Day of January, 1995

*Attest:*

BRUCE LEHMAN

*Attesting Officer*     Commissioner of Patents and Trademarks